United States Patent
Butula

[11] 3,987,054
[45] Oct. 19, 1976

[54] 4,5,6,7-TETRAHYDROBENZIMIDAZOLES
[75] Inventor: Ivan Butula, Zagreb, Yugoslavia
[73] Assignee: Pliva Pharmaceutical and Chemical Works, Zagreb, Yugoslavia
[22] Filed: Sept. 23, 1970
[21] Appl. No.: 74,866

[52] U.S. Cl. ............................... 260/309; 252/390; 252/401; 260/45.8 N; 260/247.2 B; 260/247.5 E; 260/268 BC; 260/293.6; 424/180
[51] Int. Cl.² ...................................... C07D 235/12
[58] Field of Search ............................... 260/309

[56] References Cited
FOREIGN PATENTS OR APPLICATIONS
2,003,995  11/1969  France .............................. 260/309
1,260,294  1/1972  United Kingdom ................ 260/309

OTHER PUBLICATIONS
Shen et al., Chem. Abst. 1970, vol. 73, No. 25468d.
Weidenhagen et al., Berichte 1938, vol. 71, pp. 2124–2134.

*Primary Examiner*—Natalie Trousof
*Attorney, Agent, or Firm*—Karl F. Ross; Herbert Dubno

[57] ABSTRACT
Corrosion inhibitors and preservatives of the following formula

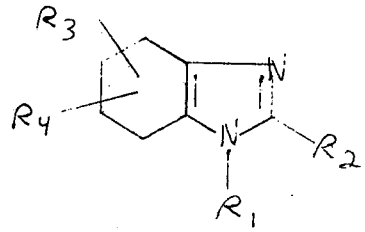

wherein
$R_1$ is hydrogen;
$R_2$ is selected from the group which consists of hydrogen, the diacetoxypropionic acid methyl ester and the diacetoxypropionic acid dialkylaminoethylamide with 1 to 4 carbon atoms in the alkyl group;
$R_3$ is hydrogen, unbranches or branched alkyl with 1 to 10 carbon atoms, carboxyl or alkoxycarbonyl wherein the alkoxy contains from 1 to 4 carbon atoms; and
$R_4$ is hydrogen, unbranched or branched alkyl with 1 to 4 carbon atoms; or acid addition or quaternary ammonium salts thereof.

3 Claims, No Drawings

4,5,6,7-TETRAHYDROBENZIMIDAZOLES

FIELD OF THE INVENTION

My present invention relates to 4,5,6,7-tetrahydrobenzimidazoles.

BACKGROUND OF THE INVENTION

The difficulties of the catalytic hydrogenation of benzimidazoles are known;
cf. Fries et al., *Liebigs Annalen der Chemie*, 550 (1942), p.33;
R. Weidenhaben and H. Wegner were not able to hydrogenate benzimidazole with nickel over diatomite and activated with molybdenum;
cf. *Reports of the German Chemical Society* 71 (1938) p. 2124. This was confirmed by H. Hartmann and L. Panizzon;
cf. *Helv. Chim. Acta* 21 (1938) p. 1962. The benzimidazole could be hydrogenated neither with nickel under high pressure at 200° C, nor with platinum at 100° C in the presence of various solvents. Harmann and Panizzon, however, were able to hydrogenate the derivative substituted in the 2-position, i.e. the 2-methyl-,2-ethyl-,1,2-dimethyl- and 2-phenyl-benzimidazoles with platinum in acetic acid (according to R. Adams' method) to the corresponding 4,5,6,7-tetrahydrobenzimidazoles. The hydrogenation of benzimidazoles substituted only in the 1-position as well as of benzimidazoles substituted in the 2-position which also carry substituents in the benzene nucleus of the benzimidazole was not possible with this method.

Hartmann and Panizzon concluded from their experiments that the hydrogenation of benzimidazoles is perfectly possible in some cases but that its success depends on the catalyst used and on the position of the substituents. R. Weidenhagen and H. Wegner loc. cit., prepared by total synthesis 4,5,6,7-tetrahydrobenzimidazole as well as 4,5,6,7-tetrahydrobenzimidazole substituted in 2-position by an alkyl group, or a phenyl-, furyl-, or anisyl group. Further, R. Weidenhagen and H. Wegner, loc. cit., prepared by total synthesis 5-methyl-4,5,6,7-tetrahydrobenzimidazole and its derivatives substituted in the 2-position by a methyl, ethyl, and n-propyl group.

W. Ried and J. Patschorke, *Liebigs Annalen der Chemie*, 616 (1958), p. 87 tried to hydrogenate dibenzimidazolylalkanes with Raney nickel under an $H_2$ pressure of 110–120 atmospheres and at 220°–230° C. After analysis it could not be definitely determined whether 6 or 8 hydrogen atoms had penetrated into the molecule.

OBJECTS OF THE INVENTION

An object of the invention is to make available new 4,5,6,7-tetrahydrobenzimidazoles.

A further object of the invention is the provision of a new method for the preparation of known and hitherto unknown 4,5,6,7-tetrahydrobenzimidazoles which is technically simple as well as rapid and produces good yields.

Another object of the invention is to make available new acid addition salts and quaternary ammonium salts of the tetrahydrobenzimidazoles and to present a method for their preparation.

An object of my invention also is to provide improved corrosion inhibitors, acid passivators, preservatives for deterioration inhibitors, age-resisting agents in mineral oils, lubricating oils, fuel oils and rubber, as intermediate products in the production of drugs, dyes, for example azo dyes, agrochemicals, dyeing auxiliary agents, polymerization catalysts for isocyanate reactions and as hardeners for epoxy resins. The quaternary ammonium salts are appropriate as tensides (surface-tension modifiers).

SUMMARY AND SPECIFIC DESCRIPTION OF THE INVENTION

The new 4,5,6,7-tetrahydrobenzimidazoles have the general formula I

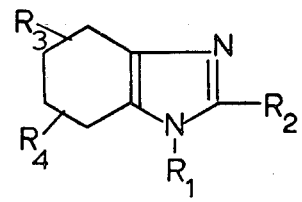

in which:

$R_1$ is a hydrogen atom;
an unbranched or branched alkyl group with 1 to 18 carbon atoms (C-atoms), preferably 1 to 4 C-atoms;
a hydroxyalkyl or carboxyalkyl group with 1 to 4 C-atoms in the alkyl group;
a 5- or 6- member cycloalkyl, alkylcycloalkyl, or cycloalkylalkyl group;
an arylalkyl group with 1 to 4 C-atoms in the alkyl group; a glucosyl, arabinosyl, xylosyl, ribosyl or another sugar group derived from hexoses, pentoses or tetroses; or
the group A-Z in which A is an unbranched or branched alkylene group with 1 to 4 C-atoms and Z is an amino, lower monoalkylamino, lower dialkylamino, morpholino, N-pyrrolidino, N-piperidino, N-piperazino, N'-lower alkyl-N-piperazino, N'-(ω-hydroxyalkoxy-lower-alkyl)-N-piperazino group;

$R_2$ is a hydrogen atom;
an unbranched or branched alkyl group with 1 to 20 C-atoms;
the trifluormethyl, hydroxymethyl or carboxyl group or
a carboxylalkyl group with 1 to 4 C-atoms;
a dialkylaminoethylaminocarbonylalkyl, dialkylaminoethylaminocarbonyl or dialkylaminoethoxycarbonylalkyl group with 1 to 4 C-atoms in the alkyl moiety;
the group of the dihydroxypropionic acid, of the diacetoxypropionic acid methyl esters, or of the diacetoxylpropionic acid dialkylaminoethylamide with 1 to 4 C-atoms in the alkyl group;
the group of the tetrahydroxylvaleric acid;
a polyhydroxyalkyl group with 4 to 6 C-atoms, the cyclopentyl or cyclohexyl group, an alkylcyclohexyl group with 1 to 4 C-atoms in the alkyl group;
the carboxycyclohexyl group;
the 2-,3- or 4-piperidyl group;
a phenyl, mono- or dialkylphenyl group with 1 to 4 C-atoms in the alkyl group;

a mono- or dialkoxyphenyl, mono- or dialkoxybenzyl or mono- or dialkoxyphenylethyl group with 1 to 4 C-atoms in the alkoxy moiety;

a 3,4-methylenedioxyphenyl, 3,4-methylenedioxybenzyl, or 3,4-methylenedioxyphenylethyl group;

a tetrahydrofuryl group;

an acylaminophenyl group in which the acyl moiety is derived from an aliphatic carbonic acid with 1 to 3 C-atoms;

the fluorphenyl group;

the 4,5,6,7-tetrahydrobenzimidazolyl-(2)-1,2-dihydroxyethyl or 4,5,6,7-tetrahydrobenzimidazolyl-(2)-1,2,3,4-tetrahydroxybutyl group;

an imidazolylalkyl, triazolylalkyl or tetrazolylalkyl group with 1 to 4 C-atoms in the alkyl group;

$R_3$ is a hydrogen atom;

an unbranched or branched alkyl group with 1 to 18 C-atoms, preferably 1 or 2 C-atoms, a carboxyl group or an alkoxycarbonyl group with 1 to 4 C-atoms in the alkoxy group; and $R_4$ is a hydrogen atom or an unbranched or branched alkyl group with 1 to 4, preferably 1 or 2 C-atoms, except for 4,5,6,7-tetrahydrobenzimidazole, and the 2-methyl, 5-methyl, 1,2-dimethyl, 2,5-dimethyl, 2-ethyl, 2-ethyl-5-methyl, 2-n-propyl-5-methyl-2-isopropyl, 2-isobutyl, 2-hexyl, 2-cyclohexyl, 2-phenyl and 2-anisyl derivatives of 4,5,6,7-tetrahydrobenzimidazole.

The expressions "lower alkyl group", "lower alkylene group", "lower alkylamino", "lower dialkylamino" or "lower alkylenediamino group" refer to groups with 1 to 8 C-atoms.

The salts of the 4,5,6,7-tetrahydrobenzimidazoles are salts of inorganic or organic acids, as well as the quaternary ammonium salts. Examples of inorganic acids appropriate for salt formation are the halogen hydroacids, sulfuric acid, phosphoric acid, nitric acid and perchloric acid. Examples of appropriate organic acids are acetic acid, propionic acid, oxalic acid, maleic acid, succinic acid, alkyl and alkenylsuccinic acids, aliphatic, cycloaliphatic and aromatic sulfonic acids, such as petroleum sulfonic acids, mahagony sulfonic acids, p-toluenesulfonic acid and p-docedylbenzenesulfonic acid and picric acid. The quaternary ammonium salts are derived from the usual alkylating agents, such as alkyl, cycloalkyl or arylalkyl halides, for example methyl bromide and ethyl iodide, or dialkyl sulfates.

The invention concerns also a new method for the preparation of known (the exception previously given) and previously unknown 4, 5, 6, 7-tetrahydrobenzimidazoles of the general formula I given earlier, and of their salts with acids and quaternary ammonium salts.

In the method of the invention, a benzimidazole of the general formula II

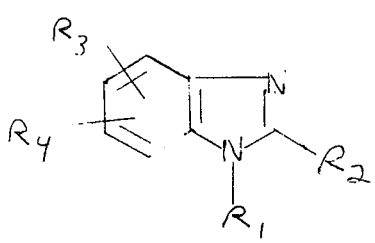

in which $R_1$, $R_2$, $R_3$ and $R_4$ have the above-stated meaning or are their hydrogenatable unsaturated precursors either a. in the form of the acid addition salt or b. in the form of the free base and in presence of at least 1 equivalent acid per basic group, is hydrogenated in presence of rhodium or of combination catalysts containing a predominance of rhodium. The thus-obtained salt of the 4, 5, 6, 7-tetrahydrobenzimidazole can then be converted in the usual manner into the free base, and possibly the free base converted into an acid addition salt and/or quaternary ammonium salt by reaction with an inorganic or organic acid or an alkylating agent.

The new method of the invention for the preparation of 4, 5, 6, 7-tetrahydrobenzimidazole derivatives runs according to the following reaction scheme:

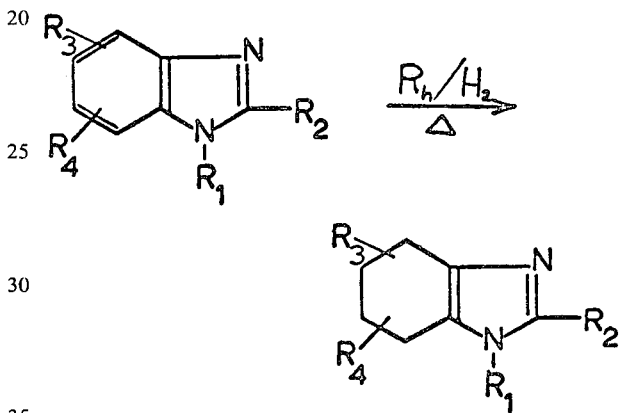

As long as the groups $R_1$, $R_2$, $R_3$ and $R_4$ are or carry hydrogenatable groups, they can also be hydrogenated under certain conditions.

The new method of the invention concerns a benzimidazole-benzene-nucleus hydrogenation, without any substitution effect. Other aromatic groups which may be present are not attacked at normal pressure or are attacked only with great difficulty. At higher reaction temperatures the 4, 5, 6, 7-tetrahydrobenzimidazole derivatives can usually be prepared with interruption of the hydrogenation at the calculated quantity of absorbed hydrogen. With further hydrogenation, the other aromatic groups can also be hydrogenated. Thus, for example, according to the method of the invention 2-[p-tert.-butylphenyl]-benzimidazole is hydrogenated to 2-[p-tert.-butylphenyl],5,6,7-tetrahydrobenzimidazole, at 80° C and a pressure of 1 kg/cm². With complete hydrogenation at 120° C and 50 kg/cm² the 2-[4-tert.-butylcyclohexyl]-4,5,6,7-tetrahydrobenzimidazole is obtained. In the hydrogenation of 2-pyridylbenzimidazole according to the method of the invention, the pyridine nucleus first and then the benzene nucleus is saturated.

Since rhodium shows no tendency toward hydrogenolysis, benzimidazoles which carry alkoxyphenyl substituents can also be hydrogenated according to the method of the invention.

Thus the 2-[4-methoxyphenyl], 2-[4-methoxyphenyl]-2-[4-methoxycyclohexyl], 2-[3-methoxyphenyl], 2-[3-methoxycyclohexyl], 2-[2-methoxyphenyl], 2-[2-methoxycyclohexyl], 2-[4-ethoxyphenyl], 2-[4- ethoxycyclohexyl], 2-[4-isopropoxyphenyl], 2-[4-isopropoxycyclohexyl], 2-[4-butoxyphenyl], 2-[4-butoxycyclohexyl], 2-[3,5-dimethoxyphenyl], 2-[3,5-diethoxyphenyl], or 2-[3,4-methylenedioxyphenyl], 2-[3,4-dimethoxycyclohexyl], 2-[3,4-dimethoxyphenylmethyl] and 2-[3,4-dimethoxyphenylethyl] derivatives of 4,5,6,7-tetrahydrobenzimidazole can be prepared. Conventional rhodium catalysts alone or on carriers can be used as catalysts in the method of the invention. Rhodium catalysts on carriers are preferred. Examples of appropriate carrier substances are silicic acid, diatomite, aluminum oxide, pumice, asbestos, carbon, titanium dioxide, barium sulfate, vermiculite and silica gel. Favored carriers are activated carbon, barium sulfate, titanium dioxide, aluminum oxide and silica gel. The carrier catalysts shall contain rhodium in proportions of 2 to 10%. The catalysts can be used several times after thorough washing with for example, water, methanol, or acetic acid.

The method of the invention is carried out in a solvent or diluent in which the benzimidazole is at least partly soluble. Examples of adequate solvents are water, acetic acid, propionic acid, lower aliphatic alcohols, glycol ether, diethyl ether, tetrahydrofuran or their mixtures.

The method of the invention can be carried out within a relatively wide range of temperatures at normal (atmospheric) pressure or excess (superatmospheric) pressure. The preferred temperature range at normal pressure goes from about 0° C to the boiling point of the solvent or diluent utilized. When working under excess pressure, any aromatic substituents which may be present can also be hydrogenated. The hydrogenation can be carried out at pressures going from normal (atmospheric) pressure to about 120 kg/cm$^2$ or more. The hydrogenation can also be carried out at higher temperatures if the compounds to be hydrogenated or the hydrogenation products allow or require it. Some substituted benzimidazole compounds can change at higher reaction temperatures. For example the temperature in the hydrogenation of benzimidazolyl(2)-acetic acid should not exceed 80° C, since a decarboxylation takes place at higher temperatures and 2-methyl-4,5,6,7-tetrahydrobenzimidazole is then obtained.

The following Table I shows the results of the hydrogenation of benzimidazole with the use of various catalysts. Hartmann and Panizzon's finding that platinum does not hydrogenate benzimidazole even at higher pressure and temperature (Experiments 1, 2, 3 and 8) is confirmed.

The mixed Rh/Pt catalyst recommended for the nucleus hydrogenation (cf. F. Zymalkowski, *Catalytic Hydrogenation In Anchemico-Organic Laboratory*, Ferd. Enke Verlag, Stuttgart, 1965, p. 28) was also inferior to rhodium. A part of the benzimidazole was hydrogenated quite slowly and the hydrogenation stopped after 20 hours. (Example No. 4).

Only when using the rhodium catalyst can benzimidazole be hydrogenated, slowly but completely at normal pressure (Examples 5–7), rapidly and easily at higher pressure and temperature (Example 9).

An important part of the invention deals with the correct choice of corresponding "solvents". Other than acetic acid or other lower carbonic acids, water or other polar solvents such as lower aliphatic alcohols, glycol ether, diethylether or tetrahydrofuran can be used, if the compound to be hydrogenated is used in the form of its salt with an inorganic or organic acid, or if these acids are added to this solvent in a proportion of at least 1 equivalent per basic group. If an insufficient quantity of acid is used, no hydrogenation takes place or the hydrogenation is incomplete (Table II).

In water no hydrogenation takes place at normal pressure. At higher pressure and higher temperature, the hydrogen is absorbed very slowly, but the hydrogenation process stops after a certain time (Table II, Example 1). The same result is obtained when only one part benzimidazole is converted into the hydrochloride, in spite of great rapidity at the beginning (Example 2). After addition of 1 mole equivalent HCl, the hydrogenation is fast and complete (Example 3); with excess HCl, the hydrogenation is even more rapid (Example 4).

Table III shows the influence of various acid-solvent systems on the hydrogenation rate.

Table III shows that the hydrogenation rate depends on the kind of "solvent" used but also on the temperature and pressure.

From this appear the best and most economical hydrogenation conditions for the method of the invention. The hydrogenation should preferably be carried out with Rh-carrier catalysts in glacial acetic acid, diluted acetic acid or water, under addition of at least equimolar quantities of strong acids (for example HCl, $H_2SO_4$, etc.), all present basic nitrogen groups being neutralized by the acid, while acid can be present in excess at a temperature of 20° to 120° C and at a hydrogen pressure of 1–8 kg/cm$^2$. A particularly economical method is the hydrogenation in water under addition of strong acids at higher pressure and temperatures. In the method of the invention the salts of the tetrahydrobenzimidazoles are thus formed. The hydrogenation methods A to D, discussed below, can be used to obtain the free base. Methods A and B are appropriate to obtain the tetrahydrobenzimidazoles which do not form salts with bases. The tetrahydro benzimidazoles which form salts with bases are processed according to methods C and D. Parts are by weight unless otherwise indicated.

Hydrogenation Methods

A. 1 part of the compound to be hydrogenated is hydrogenated with 0.01 to 1 part of a 5%-rhodium carrier catalyst in 10 to 20 parts solvent at normal pressure in a flask provided with a magnetic stirrer, or at higher pressure, in an autoclave. Reaction temperatures and pressures are shown on Table IV.

Once the calculated quantity of hydrogen has been absorbed, the catalyst is filtered off, and the filtrate is concentrated. The residue is then dissolved in water, made alkaline with soda lye (NaOH) and the hydrogenation product is filtered off or if necessary, extracted with a solvent. The raw product is recrystallized from an appropriate solvent.

B. The hydrogenation is carried out as under A. The catalyst is filtered off and the filtrate is concentrated. The residue is dissolved in water, the solution make alkaline and the hydrogenation product is extracted with chloroform, trichloroethylene, benzene or other solvents which do not mix with water. The extract is then dried over a drying agent, the solvent is distilled off, and the liquid product distilled in high vacuum or converted into the hydrochloride.

C. Hydrogenation as under (A)

Once the catalyst has been filtered off and the solvent has been concentrated, the residue is diluted with water and mixed with alkali in a quantity equivalent to the quantity of acid present during hydrogenation. After cooling, the precipitated hydrogenation product is filtered off.

D. After the catalyst has been filtered off, the filtrate is concentrated, the quantity of alkali equivalent to the inorganic acid is added and the solution is evaporated until dry. The residue is extracted with methanol or acetone, the extract concentrated, and if the hydrogenation product does not crystallize, it is then precipitated with ether or another appropriate solvent.

Method for the Preparation of Quaternary Ammonium Salts

E. For tetrahydrobenzimidazoles of the general formula II, in which $R_1$ is not hydrogen:

1 mole of the tetrahydro compound is dissolved in a little methanol and the solution is mixed with 1 mole of an alkyl, cycloalkyl or arylalkyl halide and allowed to react either for a long time at room temperature or for a short time under heating. Once the solvent has been distilled, the quaternary ammonium salt remains in almost pure form.

F. For tetrahydrobenzimidazoles of the general formula II in which $R_1$ is a hydrogen atom:

1 mole tetrahydro compound is as in (E) permitted to react with 1 mole of an alkyl, cycloalkyl or arylalkyl halide. Then 1.1 mole sodium hydroxide is added and the reaction mixture is heated for an hour under reflux. After a new addition of 1 mole alkyl, cycloalkyl or arylalkyl halide, the mixture is boiled for an hour more under reflux, and then the precipitated sodium salt is filtered off and the solvent is distilled. The quaternary ammonium salt is left. The conversion proceeds according to the following schema:

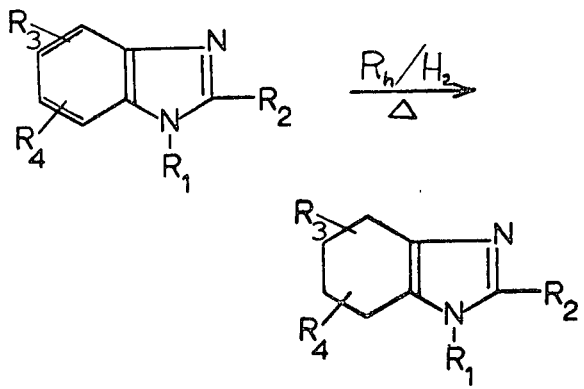

The preparation of hitherto unknown original compounds is explained in Examples 1 to 6.

EXAMPLE 1

Preparation of 5- or 6-carboxy-benzimidazole-methyl ester 2 g of 5- or 6-carboxy-benzimidazole are boiled for an hour under reflux in 10 ml thionyl chloride. The excess thionyl chloride is distilled off and the residue is dissolved in methanol. After evaporation of the methanol, the residue is treated with diluted ammonia and taken up in chloroform. The product is precipitated with ligroin (benzene). Yield quantitative, m.p. 134°–136° C.

EXAMPLE 2

Preparation of benzimidazolyl-2-acetic acid-diethylaminoethylamide 19 g benzimidazolyl-2-acetic acid methyl ester and 12 g diethylamino-ethylamine are heated for 30 min. to 80°–90° C. After cooling the reaction mixture is mixed with ether and the precipitated product is filtrated. After recrystallization from a mixture of benzene and ligroin 16.2 g product of m.p. 119°–121° C are obtained.

EXAMPLE 3

Preparation of 3-benzimidazolyl-2-propionic acid-diethylaminoethylamide 3.8 g benzimidezolyl-propionic acid are dissolved under stirring in 10 ml thionyl chloride. After conversion, the excess of thionyl chloride is evaporated, the residue is mixed with dry benzene and ligroin and filtered off. 3.7 g acid chloride of m.p. 100°–103° C are obtained (decomposition).

This acid chloride is added under stirring to a solution of 4.6 g diethylamino-ethylamine in 10 ml acetone, stirred for 10 min. and evaporated until dry. The residue is dissolved in water, made alkaline with NaOH and extracted with acetic ester. After recrystallization from a mixture of acetic ester and ligroin, 4.8 g product of m.p. 261°–263° C are obtained.

EXAMPLE 4

Preparation of 3-benzimidazolyl-2-propionic acid-diethylaminoethyl ester 2 g benzimidazolyl-propionic acid are converted by brief boiling in acetic acid anhydride into the cyclic amide. 0.7 g of this compound and 1.0 g diethylaminoethyl alcohol are heated for 15 min. to 120° C, the melted substance is dissolved in ethylacetate ester and the solution is washed three times with water. After drying over sodium sulfate, the solvent is distilled and the semi-solid residue is used for hydrogenation without further purification.

EXAMPLE 5

Preparation of 3-benzimidazolyl-(2)-2,3,-diacetoxy-propionic acid diethylamino-ethylamide 3-benzimidaxolyl-(2)-2,3-dihydroxy-propionic acid is converted into the N,N'-diacetylated cyclic amide by brief boiling in acetic anhydride. 3 g of this compound are then boiled in 30 ml benzene and 1.3 g diethylaminoethylamine for 1 hour under reflux, concentrated and the product is precipitated with ligroin. Yield: 80% of theoretical, m.p. 140° C.

EXAMPLE 6

Preparation of 3-benzimidazolyl-(2)-2,3,-diacetoxy-propionic acid methyl ester

The cyclic amide obtained as intermediate product in Example 5, is dissolved in methanol and heated for 1½ hours to 130° C in a bomb tube. After evaporation of the methanol the residue is recrystallized from a mixture of benzene and ligroin. Yield: 75% of the theoretical, m.p. 104° C.

Table IV shows examples of tetrahydrobenzimidazoles which can be prepared according to the method of the invention.

The tetrahydrobenzimidazoles are plainly characterized by their IR spectrum. The aromatic oscillations of the benzene nucleus (depending on the kind of substitution between 670 and 900 cm$^{-1}$), characteristic of the nonhydrogenated benzimidazoles do not appear in the hydrogenated compounds. The $^{(HN)}$ assoc. absorption (between 2400 and 3500), characteristic of the imidazole nucleus remains.

Thin-layer chromatograms of the hydrogenated compounds show, with a few exceptions, some general rules. The more basic hydrogenation products migrate through silica gel H (Merck, solvent benzene/methanol 7:3 or chloroform/methanol 8:2; spots are made visible in iodine chamber) more slowly, their $R_f$ values are smaller than those of the non-hydrogenated original compounds.

The tetrahydrobenzimidazoles prepared according to the method of the invention can be used for various purposes, for example as corrosion inhibitors, particularly for copper and copper alloys, acid passivators for iron and steel, age-resisting agents in mineral oils, fuel oils and rubber, as intermediate products in the manufacturing of pharmaceuticals, dyes, for example azo dyes, and agrochemicals, dyeing auxiliary agents, polymerization catalysts for isocyanate addition reactions and hardeners for epoxy resins. The quaternary ammonium salts of the tetrahydrobenzimidazoles possess a definite tenside effect and can be used for example to wet and soften textiles. 2-methyltetrahydrobenzimidazole has a rather good diuretic action in rabbits and dogs.

The use of 4,5,6,7-tetrahydrobenzimidazoles as age-resisting agents for rubber, as metal deactivators in lubricating oils and as anti-corrosive for iron is explained by means of a few examples.

Age-resistant effect in rubber

The vulcanization batches of the following composition were vulcanized for 20 min. at 153° C in a press.

| a) Test mixture | Parts |
| --- | --- |
| Natural caoutchouc (light crepe) | 100 |
| ZnO | 10 |
| Stearic acid | 1 |
| BaSO$_4$ | 75 |
| TiO$_2$ - anatase | 10 |
| Sulfur | 3 |
| Diphenylguanidine (accelerator) | 0.5 | b as (a) + 2 parts of compound No. 16 (2-[4-tert.butylphenyl] -4,5,6,7-tetrahydrobenzimidazole)

d. as (a) + 2 parts of compound No. 17 (2-[4-tert.-butylcyclohexyl] -4,5,6,7-tetrahydrobenzimidazole). After vulcanization and aging the following mechanico-technological properties were found:

|  | a) (blank sample) | b) | c) | d) |
| --- | --- | --- | --- | --- |
| Properties before aging |  |  |  |  |
| Hardness(Sh A) | 47 | 49 | 50 | 55 |
| elasticity % | 62 | 65 | 65 | 70 |
| 100 % modulus kp/cm$^2$ | 10 | 11 | 12 | 17 |
| 500 % modulus kp/cm$^2$ | 22 | 22 | 28 | 52 |
| tensile strength to breakage | 190 | 197 | 208 | 195 |
| kp/cm$^2$ |  |  |  |  |
| breaking tension % | 750 | 730 | 690 | 600 |
| Properties after aging in hot air (48 hts./100° C) |  |  |  |  |
| Hardness(Sh A) | 44 | 46 | 46 | 48 |
| Elasticity % | 50 | 53 | 53 | 55 |
| 100 % modulus kp/cm$^2$ | 7 | 10 | 9 | 10 |
| 500 % modulus kp/cm$^2$ | 17 | 23 | 20 | 32 |
| tensile strength to breakage kp/cm$^2$ | 36 | 60 | 70 | 82 |
| breaking tension % | 430 | 550 | 600 | 545 |
| remaining tensile strength % | 19 | 30 | 34 | 42 |
| remaining breaking tension % | 57 | 73 | 87 | 91 |
| Improvement against control sample % |  |  |  |  |
| for tensile strength % | — | 50 | 79 | 121 |
| for breaking tension % | — | 28 | 53 | 60 |

The properties of the vulcanizate were determined with the following testing standards:

tensile strength, modulus and breaking tension according to DIN 53 504, norm. p. 2 Elasticity DIN 53 512 Hardness DIN 53 505

Medal deactivation in lubricating oils

According to the ASTM testing standard D 130, a copper strip is dipped in a corrosive mineral oil containing sulfur (first raffinate SAE 10, with sulfurated sperm oil adjusted to 0.7% total sulfur) at higher temperature under addition of 0.05% of the compound to be tested.

The degree of blackening of the copper strip is the measurement of the passivating effect of the compound.

| Compound No. | Cu-activity at 100° C after | | Aspect of the sample |
| --- | --- | --- | --- |
|  | 3 hrs. | 24 hrs. |  |
| blank test sample | 4 a | 4 b | black |
| 1 | 3 a | 3 a | orange-yellow |
| 6 | 3 a | 3 a | orange-yellow |
| 16 | 3 a | 3 b | blue-green |
| 17 | 3 b | 4 a | blue-black |
| 19 | 3 a | 3 b | blue-green |
| 20 | 3 a | 3 a | orange-yellow |

Similar results were found in gear oils which contained salts of alkyldithiophosphates as well as sulfurated sperm oil.

Iron anticorrosive

The tetrahydrobenzimidazoles in the form of petroleumsulfo acid salts have an excellent anticorrosive action on iron.

Steel plates (DIN 17200) are treated with mineral oil (SAE 20) containing 0.2% of an ethoxylated nonylphenol (a) and 0.8% of a tetrahydrobenzimidazole-petroleumsulfo acid salt and exposed to, as in DIN 50 017, condensed moisture-weather changes in an apparatus (cf. W. Kesternich, "Steel and Iron", 1951, No. 11, p. 587).

For comparative purposes, essential oil SAE 20 was tested with 0.2% ethoxylated nonylphenol (a) as well as essential oils containing sodium petroleum sulfonate (b) and barium petroleum sulfonate (c), which contained resp. 0.2% ethoxylated nonylphenol and 0.8% of the petroleum sulfonate. The results are shown on Table V.

Table I

Hydrogenation of 1.2 g benzimidazole in 30 ml AcOH
at normal pressure and/or of 2.4 g benzimidazole in 50 ml AcOH
at 60 atm.

| Ex. No. | Catalyst Metal g | in form of | Temp. °C pressure Atm. | Hydrogenation time hrs. 50 % of calc. $H_2$ quantity absorbed | 100 % of calc. $H_2$ quantity absorbed |
|---|---|---|---|---|---|
| 1 | 0.2 | $PtO_2$ | 80/1 | no | hydrogenation |
| 2 | 0.2 | $Pt/BaSO_4$ | 20/1 | no | hydrogenation |
|   |     |             | 80/1 | no | hydrogenation |
| 3 | 0.2 | Pt/carbon | 80/1 | no | hydrogenation |
| 4 | 0.1 | Rh/Pt 4:1 | 80 | After 20 hrs. 10 % of the benzimidazole was hydrogenated | |
| 5 | 0.1 | Rh/carbon | 80 | 16 | 35 |
| 6 | 0.1 | $Rh/TiO_2$ | 80 | 15 | undetermined |
| 7 | 0.1 | $Rh/Al_2O_3$ | 80 | 18 | undetermined |
| 8 | 0.05 | Pt/carbon | 120/60 | no | hydrogenation |
| 9 | 0.025 | Rh/carbon | 120/60 | 0.2 | 0.45 |

Table II

Hydrogenation of 2.4 g benzimidazole in 100 ml water
with 1.5 Rh/carbon (5 % Rh) at 120° C and 60 kg/cm².

| Equivalent HCl | Hydrogenation time (in hrs.) until absorption of 50 % (100 %) of the calculated hydrogen quantity |
|---|---|
| 0.1 | In 5 hrs. 20 % are hydrogenated, then the hydrogenating process stops |
| 0.5 | 20 % of theoretical $H_2$ are raidly (0.3 hrs.) absorbed, then the hydrogenating process stops |
| 1.0 | 0.20 (0.45) |
| 2.0 | 0.15 (0.3) |

Table III

Hydrogenation of benzimidazole with 5 % Rh/carbon in 30 ml
solvent at normal pressure or in 50 ml solvent at higher pressure.

| Ex. No. | benzimidazole, g | Rh-metal g | solvent | added acid | Temp. °C | pres. kg/cm² | Hydrogenation time, hrs. 50 % of calc. $H_2$-quantity abs. | 100 % of calc. $H_2$-quantity absorbed |
|---|---|---|---|---|---|---|---|---|
| 1 | 1.2 | 0.1 | water | — | 60 | 1 | no | hydrogenation |
| 2 | 1.2 | 0.1 | water | 1.1 g $HClO_4$ | 60 | 1 | 5.5 | 12 |
| 3 | 1.2 | 0.1 | ethyl alcohol | — | 60 | 1 | no | hydrogenation |
| 4 | 1.2 | 0.1 | ethyl alcohol | 0.36 g HCl | 60 | 1 | 35 | undetermined |
| 5 | 1.2 | 0.1 | 50 % acetic acid | — | 60 | 1 | 25 | undetermined |
| 6 | 1.2 | 0.1 | 99.9 % acetic acid | — | 60 | 1 | 20 | undetermined |
| 7 | 1.2 | 0.1 | 99.9 % acetic acid | 0.5 g $H_2SO_4$ | 60 | 1 | 7.0 | undetermined |
| 8 | 1.2 | 0.1 | 99.9 % acetic acid | 1.1 g $HClO_4$ | 60 | 1 | 4.0 | 9.0 |
| 9 | 5.7 | 0.05 | ethyl alcohol | — | 120 | 50 | no | hydrogenation |
| 10 | 5.7 | 0.05 | dioxan | — | 120 | 50 | no | hydrogenation |
| 11 | 5.7 | 0.05 | water | — | 120 | 50 | In 5 hrs. 30 % of the benzimidazole are hydrogenated, then the hydrogenation came to a stop. | |
| 12 | 5.7 | 0.05 | water | 5.5 g HCl (Conc.) | 120 | 50 | 0.18 | 0.40 |
| 13 | 5.7 | 0.05 | acetic acid | — | 120 | 50 | 0.25 | 0.5 |
| 14 | 5.7 | 0.05 | acetic acid | 5.5 g $HClO_4$ | 120 | 50 | 0.15 | 0.35 |

Table IV

| Original conditions | | | | Hydrogenation conditions | | | |
|---|---|---|---|---|---|---|---|
| $R_1$ | $R_2$ | $R_3$ | $R_4$ | Method | catalyst | acid-solvent system | Temp., °C pres. kg/cm² |
| H | H | H | H | A | Rh/carbon | AcOH | 120/50 |
| $(C_2H_5)_2N-C_2H_4-$ | H | H | H | B | Rh/carbon | 60% AcOH + HCl | 120/50 |
| H | $CH_3$ | H | H | A | $Rh/TiO_2$ | 60% AcOH $H_2SO_4$ | 120/70 |
| $(C_2H_5)_2N-C_2H_4-$ | $CH_3$ | H | H | B | Rh/carbon | AcOH + HCl | 100/60 |
| H | $CH_3$ | 6-$CH_3$ | H | A | Rh/carbon | AcOH + $HClO_4$ | 120/60 |
| H | $C_2H_5$ | H | H | A | $Rh/Al_2O_3$ | 50% AcOH + $H_2SO_4$ | 80/1 |
| H | $C_{17}H_{34}$ | H | H | A | Rh/carbon | AcOH + $HClO_4$ | 120/60 |
| H | H | 5-$CH_3$ | H | A | Rh/carbon | 1n HCl | 120/60 |

Table IV-continued

| | | | | | | | |
|---|---|---|---|---|---|---|---|
| H | CF$_3$ | H | H | A | Rh/carbon | AcOH + HClO$_4$ | 80/1 |
| H |  | H | H | A | Rh/carbon | 50% AcOH + HCl | 120/50 |
| |  | H | H | A | Rh/TiO$_2$ | 50% AcOH | 120/60 |
| (C$_2$H$_5$)$_2$NC$_2$H$_4$ | 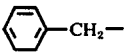—CH$_2$— | H | H | B | Rh/carbon | 60% AcOH + HCl | 80/1 |
| H | 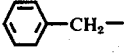—CH$_2$— | H | H | A | " | AcOH | 120/60 |
| H | 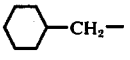—CH$_2$— | H | H | A | " | 50% AcOH + H$_2$SO$_4$ | 120/60 |
| H | CH$_3$CONH—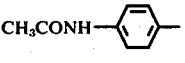— | H | H | A | " | AcOH | 120/60 |
| H | (CH$_3$)$_3$C—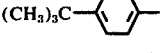— | H | H | A | Rh/carbon | AcOH + HClO$_4$ | 80/1 |
| H | (CH$_3$)$_3$C—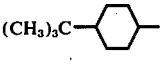— | H | H | A | " | AcOH + HClO$_4$ | 120/60 |
| H | H$_3$C—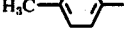— | H | H | A | " | AcOH + H$_2$SO$_4$ | 80/1 |
| H | H$_3$C—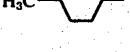— | H | H | A | " | H$_2$O + H$_2$SO$_4$ | 120/60 |
| H | 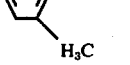 | H | H | A | " | AcOH + H$_2$SO$_4$ | 80/1 |
| H | 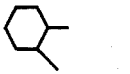 | H | H | A | " | AcOH + H$_2$SO$_4$ | 120/60 |
| H | 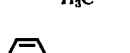 | H | H | C | " | AcOH + HCl | 120/60 |
| H | —COOH | H | H | C | " | H$_2$O + HCl | 60/120 |
| H | —CONHC$_2$H$_4$N(C$_2$H$_5$)$_2$ | H | H | A | Rh/carbon | 50% AcOH + HCl | 60/60 |
| H | H | 5-COOH | H | D | " | 50% AcOH + HCl | 120/60 |
| H | H | 5-COOCH$_3$ | H | A | " | AcOH + H$_2$SO$_4$ | 80/60 |
| H | —CH$_2$COOH | H | H | D | " | 50% AcOH + HCl | 50/60 |
| H | —CH$_2$CONHC$_2$H$_4$N(C$_2$H$_5$)$_2$ | H | H | A | " | AcOH | 50/60 |
| H | —(CH$_2$)$_2$—COOH | H | H | D | " | H$_2$O + HCl | 120/60 |
| H | —(CH$_2$)$_2$CONHC$_2$H$_4$N(C$_2$H$_5$)$_2$ | H | H | A | " | 50% AcOH + HCl | 120/60 |
| H | —(CH$_2$)$_2$CO$_2$C$_2$H$_4$N(C$_2$H$_5$)$_2$ | H | H | A | Rh/TiO$_2$ | AcOH + HCl | 80/60 |
| H | —CH$_2$OH | H | H | A | Rh/carbon | AcOH | 80/1 |
| H | —(CHOH)$_2$COOH | H | H | D | " | 50% AcOH + H$_2$SO$_4$ | 120/60 |

Table IV-continued

| R₁ | R₂ | R₃ | R₄ | Method | | Solvent | Temp/Time |
|---|---|---|---|---|---|---|---|
| H | —(CHOAc)₂CONHC₂H₄N(C₂H₅)₂ | H | H | A | " | AcOH + HCl | 120/60 |
| H | —(CHOAc)₂COOCH₃ | H | H | A | " | AcOH + HClO₄ | 120/60 |
| H | —(CHOH)₄—COOH | H | H | C | " | H₂O + H₂SO₄ | 120/60 |
| H | benzimidazol-2-yl—CH(OH)—CH(OH)— | H | H | A | " | AcOH + H₂SO₄ | 120/60 |
| H | benzimidazol-2-yl—(CHOH)₄— | H | H | A | Rh/carbon | AcOH + HCl | 120/60 |
| H | 3-piperidyl | H | H | A | " | H₂O + H₂SO₄ | 120/60 |
| H | 3-pyridyl | H | H | A | " | H₂O + H₂SO₄ | 120/60 |
| H | 4-fluorophenyl | H | H | A | " | AcOH + HClO₄ | 80/1 |
| H | H | 5-CH₃ | 6-CH₃ | A | " | AcOH + H₂SO₄ | 120/60 |
| H | CH₃ | 4-CH₃ | 6-CH₃ | A | " | AcOH + HClO₄ | 120/60 |
| H | CH₃ | 5-CH₃ | H | A | " | " | 120/60 |
| CH₃ | CH₃ | H | H | A | " | " | 120/60 |
| H | C₂H₅ | 5-CH₃ | H | A | Rh/carbon | 50% AcOH + H₂SO₄ | 120/60 |
| H | n-C₃H₇ | H | H | A | " | " | 120/60 |
| H | n-C₃H₇ | 5-CH₃ | H | A | " | " | 120/60 |
| H | iso—C₃H₇ | H | H | A | " | " | 120/60 |
| H | iso—C₄H₉ | H | H | A | " | " | 120/60 |
| H | n-C₆H₁₃ | H | H | A | " | " | 120/60 |
| H | 4-methoxyphenyl (CH₃—O—C₆H₄—) | H | H | A | " | AcOH + HCl | 180/60 |

| Original conditions | | | | Method | Final product | No. | yield % | F °C |
|---|---|---|---|---|---|---|---|---|
| R₁ | R₂ | R₃ | R₄ | | | | | |
| H | H | H | H | A | 4,5,6,7-tetrahydro-benzimidazole | 1 | 90 | 150 |
| (C₂H₅)₂N—C₂H₄— | H | H | H | B | 1-diethylaminoethyl-4,5,6,7-tetrahydro-benzimidazole | 2 | 70 | liquid |
| H | CH₃ | H | H | A | 2-methyl-4,5,6,7-tetrahydrobenzimidazole | 3 | 85 | 224 |
| (C₂H₅)₂N—C₂H₄— | CH₃ | H | H | B | 1-diethylaminoethyl-2-methyl-4,5,6,7-tetrahydrobenzimidazole | 4 | 70 | liquid |

Table IV-continued

| R1 | R2 | R3 | R4 | Method | Name | Ex. | Yield % | MP |
|---|---|---|---|---|---|---|---|---|
| H | CH₃ | 6-CH₃ | H | A | 2,6-dimethyl-4,5,6,7-tetrahydrobenzimidazole | 5 | 90 | 185 |
| H | C₂H₅ | H | H | A | 2-ethyl-4,5,6,7-tetrahydrobenzimidazole | 6 | 85 | 200 |
| H | C₁₇H₃₄ | H | H | A | 2-heptadecyl-4,5,6,7-tetrahydrobenzimidazole | 7 | 80 | 66 |
| H | H | 5-CH₃ | H | A | 5-methyl-4,5,6,7-tetrahydrobenzimidazole | 8 | 90 | 116 |
| H | CF₃ | H | H | A | 2-trifluormethyl-4,5,6,7-tetrahydrobenzimidazole | 9 | 78 | 248 |
| H | C₆H₅— | H | H | A | 2-phenyl-4,5,6,7-tetrahydrobenzimidazole | 10 | 60 | 294 |
| H | cyclohexyl— | H | H | A | 2-cyclohexyl-4,5,6,7-tetrahydrobenzimidazole | 11 | 92 | 266 |
| (C₂H₅)₂NC₂H₄— | C₆H₅—CH₂— | H | H | B | 1-diethylaminoethyl-2-benzyl-4,5,6,7-tetrahydrobenzimidazole | 12 | 75 | liquid |
| H | C₆H₅—CH₂— | H | H | A | 1-benzyl-4,5,6,7-tetrahydrobenzimidazole | 13 | 64 | 226 |
| H | cyclohexyl-CH₂— | H | H | A | 2-cyclohexylmethyl-4,5,6,7-tetrahydrobenzimidazole | 14 | 90 | 267 |
| H | CH₃CONH—C₆H₄— | H | H | A | 2-(4-acetylaminophenyl)-4,5,6,7-tetrahydrobenzimidazole | 15 | 82 | 324 |
| H | (CH₃)₃C—C₆H₄— | H | H | A | 2-(4-tert.-butylphenyl)-4,5,6,7-tetrahydrobenzimidazole | 16 | 85 | 276 |
| H | (CH₃)₃C—C₆H₁₀— | H | H | A | 2-(4-tert.-butylcyclohexyl)-4,5,6,7-tetrahydrobenzimidazole | 17 | 75 | 273 |
| H | H₃C—C₆H₄— | H | H | A | 2-(4-tolyl)-4,5,6,7-tetrahydrobenzimidazole | 18 | 55 | 276 |
| H | H₃C—C₆H₁₀— | H | H | A | 2-(4-methylcyclohexyl)-4,5,6,7-tetrahydrobenzimidazole | 19 | 85 | 220 |
| H | 2-CH₃-C₆H₄— | H | H | A | 2-(2-tolyl)-4,5,6,7-tetrahydrobenzimidazole | 20 | 70 | 211 |
| H | 2-CH₃-C₆H₁₀— | H | H | A | 2-(2-methylcyclohexyl)-4,5,6,7-tetrahydrobenzimidazole | 21 | 90 | 257 |
| H | 2-COOH-C₆H₁₀— | H | H | C | 2-(2-carboxycyclohexyl)-4,5,6,7-tetrahydrobenzimidazole | 22 | 80 | 248 |
| H | —COOH | H | H | C | 2-carboxy-4,5,6,7-tetrahydrobenzimidazole | 23 | 78 | 218 |
| H | —CONHC₂H₄N(C₂H₅)₂ | H | H | A | 2-(Diethylaminoethylaminocarbonyl)-4,5,6,7-tetrahydrobenzimidazole | 24 | 80 | 104 |
| H | H | 5-COOH | H | D | 5-carboxy-4,5,6,7-tetrahydrobenzimidazole | 25 | 70 | 240 |
| H | H | 5-COOCH₃ | H | A | 5-methoxycarbonyl-4,5,6,7-tetrahydrobenzimidazole | 26 | 80 | 137 |

Table IV-continued

| | | | | | | | | |
|---|---|---|---|---|---|---|---|---|
| H | —CH₂COOH | H | H | D | 2-carboxymethyl-4,5,6,7-tetrahydrobenzimidazole | 27 | 65 | 154 |
| H | —CH₂CONHC₂H₄N(C₂H₅)₂ | H | H | A | 2-diethylaminoethyl-aminocarboxymethyl-4,5,6,7-tetrahydrobenzimidazole | 28 | 70 | 146 |
| H | —(CH₂)₂—COOH | H | H | D | 2-carboxyethyl-4,5,6,7-tetrahydrobenzimidazole × 1 Mol H₂O | 29 | 80 | 240 |
| H | —(CH₂)₂CONHC₂H₄N(C₂H₅)₂ | H | H | A | 2-(diethylamino-ethyl-amino-carbonylethyl)-4,5,6,7-tetrahydrobenzimidazole | 30 | 85 | 171 |
| H | —(CH₂)₂CO₂C₂H₄N(C₂H₅)₂ | H | H | A | 2-(diethylaminoethoxycarbonylethyl)-4,5,6,7-tetrahydrobenzimidazole-HCl | 31 | 68 | 216 |
| H | —CH₂OH | H | H | A | 2-hydroxymethyl-4,5,6,7-tetrahydrobenzimidazole | 32 | 90 | 206 |
| H | —(CHOH)₂COOH | H | H | D | 3-/4,5,6,7-tetrahydrobenzimidazolyl-(2)/-2,3-dihydroxypropionic acid × H₂O | 33 | 70 | 219 |
| H | —(CHOAc)₂CONHC₂H₄N(C₂H₅)₂ | H | H | A | 3-/4,5,6,7-tetrahydrobenzimidazolyl-(2)/-2,3-diacetoxypropionic acid diethylaminoathylamid | 34 | 80 | 130 |
| H | —(CHOAc)₂COOCH₃ | H | H | A | 3-/4,5,6,7-tetrahydrobenzimidazolyl-(2)/-2,3-diacetoxypropionic acid methylester | 35 | 85 | 149 |
| H | —(CHOH)₄—COOH | H | H | C | 5-/4,5,6,7-tetrahydrobenzimidazolyl-(2)/-2,3,4,5-tetrahydroxyvalerianic acid | 36 | 75 | 220 |
| H | benzimidazolyl-CH(OH)-CH(OH)- group | H | H | A | 1,2-bis-/4,5,6,7-tetrahydrobenzimidazolyl-(2)/-1,2-dihydroxyethane | 37 | 95 | 218 |
| H | benzimidazolyl-(CHOH)₄- group | H | H | A | 1,4-bis[4,5,6,7-tetrahydrobenzimidazolyl-(2)]-1,2,3,4-tetrahydroxybutane | 38 | 80 | 226 |
| H | 4-piperidinyl | H | H | A | 2-(4-piperidino)-4,5,6,7-tetrahydrobenzimidazole | 39 | 80 | 244 |
| H | 3-pyridyl | H | H | A | 2-(3-piperidino)-4,5,6,7-tetrahydrobenzimidazole | 40 | 85 | 195 |
| H | 4-fluorophenyl | H | H | A | 2-(p-fluorphenyl)-4,5,6,7-tetrahydrobenzmidazole | 41 | 70 | 216 |
| H | H | 5-CH₃ | 6-CH₃ | A | 5,6-dimethyl-4,5,6,7-tetrahydrobenzimidazole | 42 | 90 | 143 |
| H | CH₃ | 4-CH₃ | 6-CH₃ | A | 2,4,6-trimethyl-4,5,6,7-tetrahydrobenzimidazole | 43 | 95 | 201 |

Table IV-continued

| | | | | | | | | |
|---|---|---|---|---|---|---|---|---|
| H | CH₃ | 5-CH₃ | H | A | 2,5-dimethyl-4,5,6,7-tetrahydrobenzimidazole | 44 | 90 | 184 |
| CH₃ | CH₃ | H | H | A | 1,2-dimethyl-4,5,6,7-tetrahydrobenzimidazole | 45 | 85 | 42 hygroscopic |
| H | C₂H₅ | 5-CH₃ | H | A | 2-ethyl-5-methyl-4,5,6,7-tetrahydrobenzimidazole | 46 | 90 | 204 |
| H | n-C₃H₇ | H | H | A | 2-n-propyl-4,5,6,7-tetrahydrobenzimidazole | 47 | 90 | 185 |
| H | n-C₃H₇ | 5-CH₃ | H | A | 2-n-propyl-5-methyl-4,5,6,7-tetrahydrobenzimidazole | 48 | 95 | 185 |
| H | iso—C₃H₇ | H | H | A | 2-isopropyl-4,5,6,7-tetrahydrobenzimidazole | 49 | 90 | 240 |
| H | iso—C₄H₉ | H | H | A | 2-isobutyl-4,5,6,7-tetrahydrobenzimidazole | 50 | 90 | 205 |
| H | n-C₆H₁₃ | H | H | A | 2-hexyl-4,5,6,7-tetrahydrobenzimidazole | 51 | 95 | 158 |
| H | 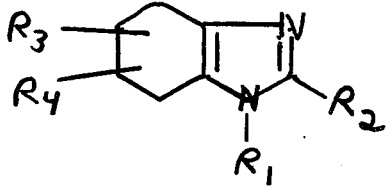 | H | H | A | 2-anisyl-4,5,6,7-tetrahydrobenzimidazole | 52 | 70 | 237 |

Table V

| Test | No. of cycles until corrosion begins | Aspect of the steel plate |
|---|---|---|
| 1 essential oil + (a) | none | corroded |
| 2 essential oil + (a) + (b) | 3 | a few spots |
| 3 essential oil + (a) + (c) | 2 | a few spots |
| 4 essential oil + (a) + compound No. 5 as petroleum sulfonate | >11 | metallic blank |
| 5 essential oil + (a) + compound No. 6 as petroleum sulfonate | >11 | metallic blank |

Tests 4 and 5 were stopped after 11 cycles without the appearance of any corrosive process (a cycle lasts 24 hours.)

I claim:
1. 3-(4,5,6,7-tetrahydrobenzamidazolyl)-(2)-2,3-diacetoxypropionic acid diethylamino-ethylamide.
2. 3-(4,5,6,7-tetrahydrobenzimidazolyl)-(2)-2,3-diacetoxypropionic acid methyl ester.
3. A compound of the following formula:

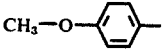

wherein:
   $R_1$ is hydrogen
   $R_2$ is selected from the group consisting of the diacetoxypropionic acid methyl ester and the diacetoxypropionic acid dialkylamino-ethylamide with 1 to 4 carbon atoms in the alkyl group;
   $R_3$ is hydrogen, unbranched or branched alkyl with 1 to 18 carbon atoms, carboxyl, or alkoxycarbonyl wherein the alkoxy contains 1 to 4 carbon atoms; and
   $R_4$ is hydrogen, unbranched or branched alkyl with 1 to 4 carbon atoms;
or acid addition or quaternary ammonium salts thereof.

* * * * *